(12) United States Patent
Chang

(10) Patent No.: US 11,213,647 B2
(45) Date of Patent: Jan. 4, 2022

(54) FULL FACE RESPIRATOR MASK

(71) Applicant: HSINER CO., LTD., Taichung (TW)

(72) Inventor: Eric Chang, Taichung (TW)

(73) Assignee: HSINER CO., LTD., Taichung (TW)

( * ) Notice: Subject to any disclaimer, the term of this patent is extended or adjusted under 35 U.S.C. 154(b) by 327 days.

(21) Appl. No.: 16/522,435

(22) Filed: Jul. 25, 2019

(65) Prior Publication Data

US 2020/0222653 A1  Jul. 16, 2020

(30) Foreign Application Priority Data

Jan. 14, 2019  (TW) .................................. 108101407

(51) Int. Cl.
*A61M 16/06* (2006.01)
(52) U.S. Cl.
CPC .... *A61M 16/0611* (2014.02); *A61M 16/0633* (2014.02); *A61M 16/0683* (2013.01); *A61M 16/0694* (2014.02)
(58) Field of Classification Search
CPC ........... A61M 16/06–0655; A61M 2016/0661; A61M 2210/0606; A61M 2210/0612; A62B 18/02; A62B 18/08; A41D 13/1161–1176; A41D 13/1184
See application file for complete search history.

(56) References Cited

U.S. PATENT DOCUMENTS

| | | | |
|---|---|---|---|
| 2002/0100479 A1* | 8/2002 | Scarberry | A61M 16/0825 128/206.24 |
| 2009/0223521 A1* | 9/2009 | Howard | A61M 16/065 128/206.23 |
| 2010/0065058 A1* | 3/2010 | Ungar | A62B 18/02 128/206.24 |
| 2010/0258133 A1* | 10/2010 | Todd | A61M 16/0825 128/207.12 |
| 2015/0034080 A1* | 2/2015 | Furuichi | A62B 18/02 128/201.19 |
| 2016/0263338 A1* | 9/2016 | Borsari | A61M 16/0683 |
| 2018/0078796 A1* | 3/2018 | Takeuchi | A62B 18/082 |

* cited by examiner

*Primary Examiner* — Valerie L Woodward
(74) *Attorney, Agent, or Firm* — Birch, Stewart, Kolasch & Birch, LLP

(57) ABSTRACT

A full face respirator mask includes a ring-shaped frame, a transparent face plate connected to an inner periphery of the frame, an air inlet extending through the face plate, and a cushion integrally molded to the frame and having an abutment portion. The frame has top, bottom, left and right parts. At least one protruding plate extends rearwardly and horizontally from the top part. The at least one protruding plate is embedded in the cushion body to push the abutment portion to abut tightly against the face of a user when the full face respirator mask is positioned on the face of the user.

8 Claims, 9 Drawing Sheets

FULL FACE RESPIRATOR MASK

CROSS-REFERENCE TO RELATED APPLICATION

This application claims priority to Taiwanese Patent Application No. 108101407, filed on Jan. 14, 2019.

FIELD

The disclosure relates to a medical equipment, more particularly to a full face respirator mask for use with a positive pressure respirator.

BACKGROUND

People with sleep apnea are usually treated with a positive pressure respirator and a mask.

Referring to FIGS. 1 and 2, an existing full face respirator mask includes a face frame 11, an air inlet 13 extending through the face frame 11 for connection with a positive pressure respirator 16, a ring-shaped cushion 12 made of silicone and connected to a rear end of the face frame 11, and a connector unit 14 connected to the face frame 11. The cushion 12 has an abutment portion 121 for abutting against the forehead of a user 22. The connector unit 14 includes two upper connectors 141 on left and right parts 113, 114 of the face frame 11, and two lower connectors 141' on the left and right parts 113, 114 of the face frame 11 below the upper connectors 141.

In use, a head strap 15 is connected to the upper and lower connectors 141, 141' to fix the existing full face respirator mask to the face of the user 22 such that the cushion 12 abuts against the face of the user 22. The face of the user 22, the face frame 11 and the cushion 12 cooperatively define a receiving space 17 communicating with the air inlet 13. The air inlet 13 is then connected to the positive pressure respirator 16, and the positive pressure respirator 16 is operated to supply pressurized gas body, such as air, oxygen, etc., into the receiving space 17 through the air inlet 13 for the user 22 to use.

However, in actual use, it is found that although the head strap 15 can be adjusted to tighten the upper and lower connectors 141, 141' so as to pull the face frame 11 toward the face of the user 22, the force that drives the center of the abutment portion 121 toward the forehead of the user 22 is small, so that it is not easy to tightly press the abutment portion 121 against the forehead of the user 22. The treatment principle of the positive pressure respirator 16 is that by supplying the pressurized gas body, the gas pressure in the receiving space 17 is higher than the atmospheric pressure so as to maintain the operation of the upper respiratory tract of the user. The pressure difference is thus likely to cause a gap 18 between the center of the abutment portion 121 and the user 22, so that the gas body in the receiving space 17 is likely to leak from the gap 18. Hence, the gas pressure in the receiving space 17 cannot be maintained to be higher than the atmospheric pressure, thereby affecting the treatment.

In this regard, some people will adjust the head strap 15 to increase the pulling force applied to the face frame 11 so as to tightly abut the abutment portion 121 against the face of the user 22 and prevent the occurrence of the gap 18. However, this method will increase the force applied to the upper connectors 141 to press two ends of the abutment portion 121 tightly against the face of the user 22, causing discomfort to the user.

SUMMARY

Therefore, an object of the present disclosure is to provide a full face respirator mask that can alleviate at least one of the drawbacks of the prior art.

Accordingly, a full face respirator mask of this disclosure includes a ring-shaped frame, a transparent face plate connected to an inner periphery of the ring-shaped frame, an air inlet extending through the transparent face plate in a front-rear direction for connection with a positive pressure respirator, a cushion made of silicone and integrally molded to the ring-shaped frame, and two upper connectors.

The ring-shaped frame has a top part corresponding to the forehead of a user, a bottom part opposite to the top part and corresponding to the chin of the user, and a left part and a right part connected between the top part and the bottom part and respectively corresponding to two cheeks of the user. The ring-shaped frame further has at least one protruding plate extending rearwardly and horizontally from the top part. The cushion has a ring-shaped cushion body cooperating with the transparent face plate to define a receiving space which communicates with the air inlet. The cushion body includes a ring-shaped abutment portion extending inwardly from an inner peripheral end of the cushion body for abutting against the face of the user. The upper connectors extend outwardly and respectively from the left and right parts in proximity to the top part and located externally of the cushion. Each upper connector has a first engaging hole for connection with a head strap unit. The at least one protruding plate is embedded in the cushion body to push the abutment portion to abut tightly against the face of the user when the full face respirator mask is positioned on the face of the user.

BRIEF DESCRIPTION OF THE DRAWINGS

Other features and advantages of the disclosure will become apparent in the following detailed description of the embodiments with reference to the accompanying drawings, of which.

DETAILED DESCRIPTION

Figure 1:
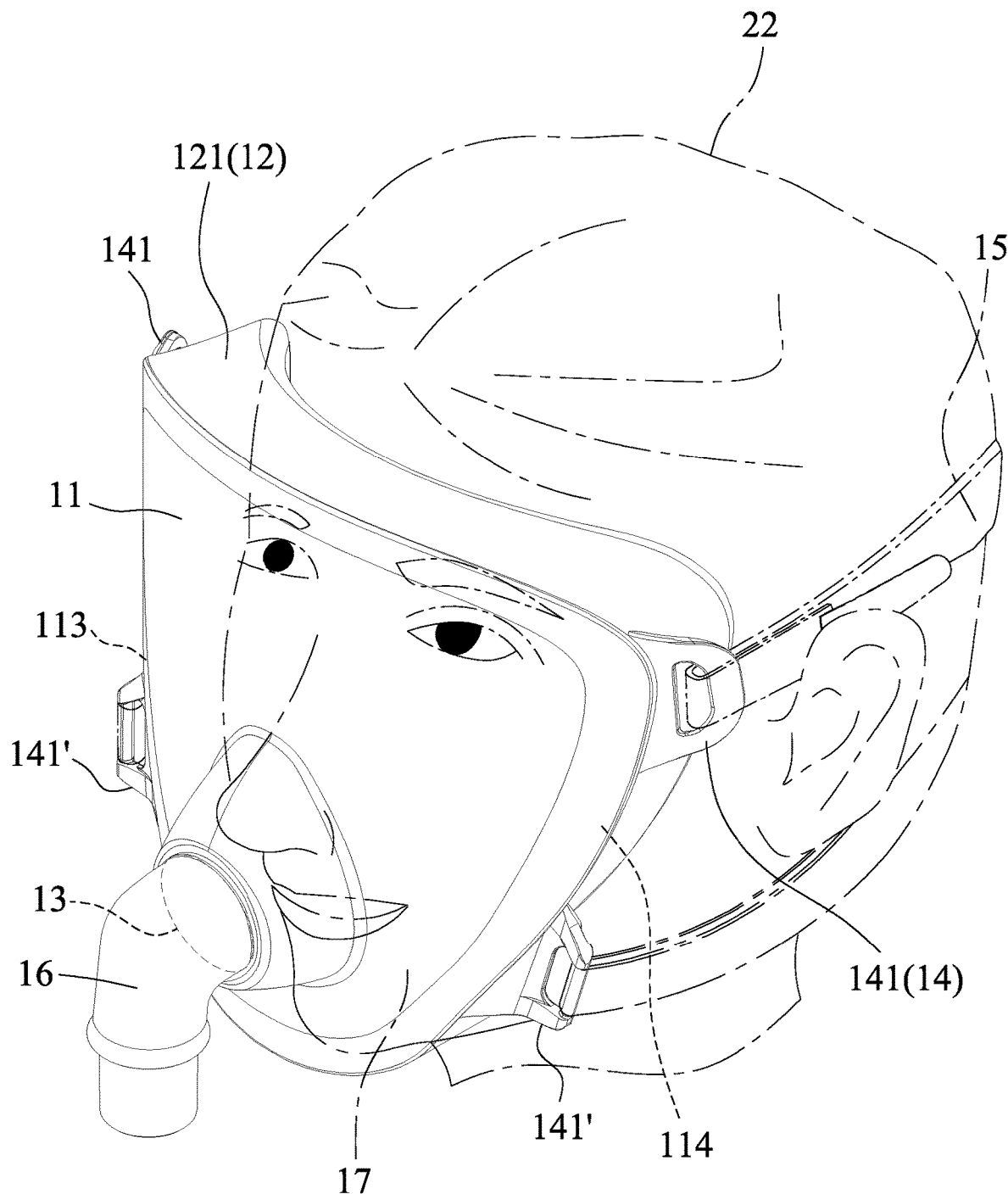
FIG. 1 is a perspective view of an existing full face respirator mask connected to a positive pressure respirator.
Figure 2:
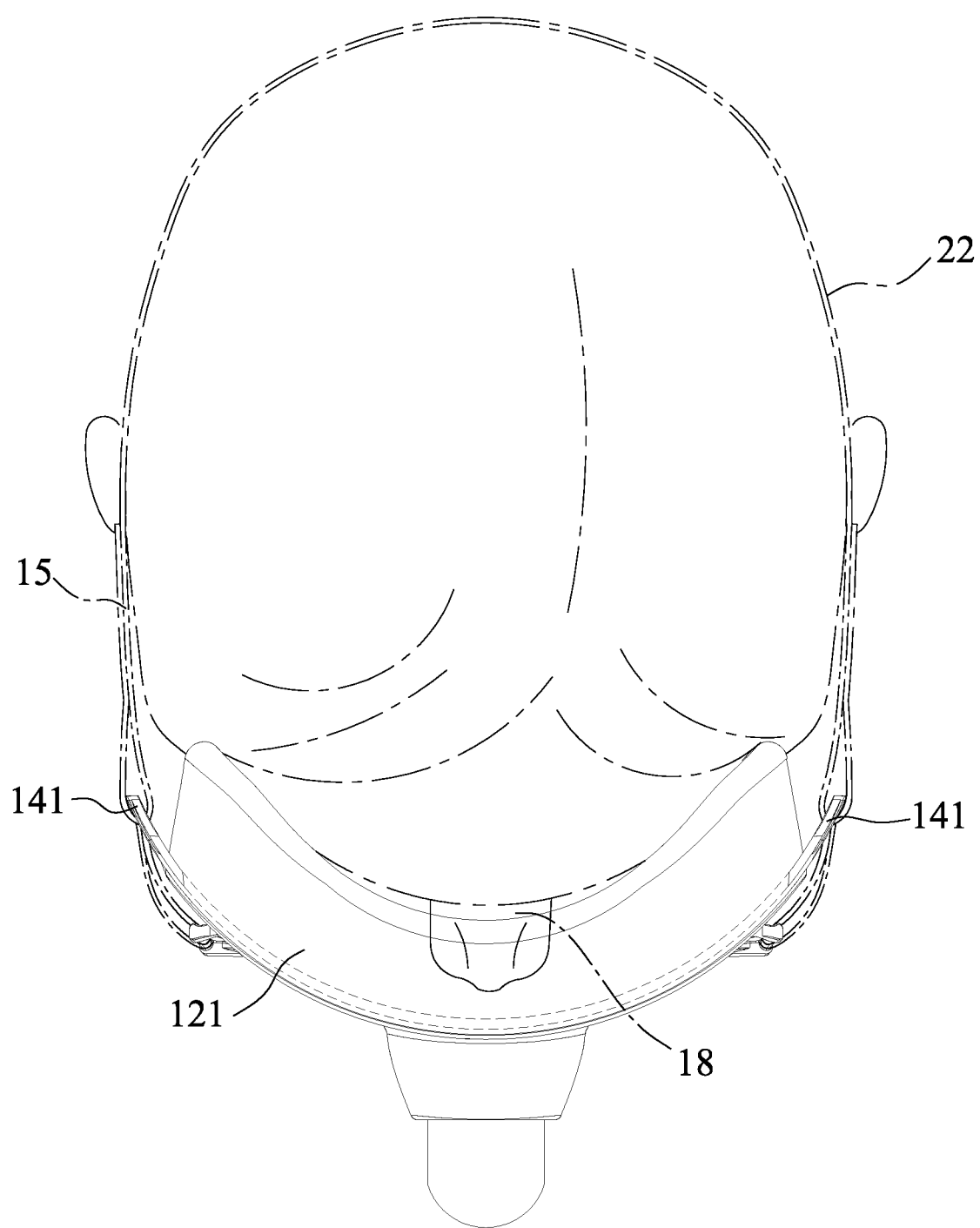
FIG. 2 is a top view of FIG. 1.
Figure 3:
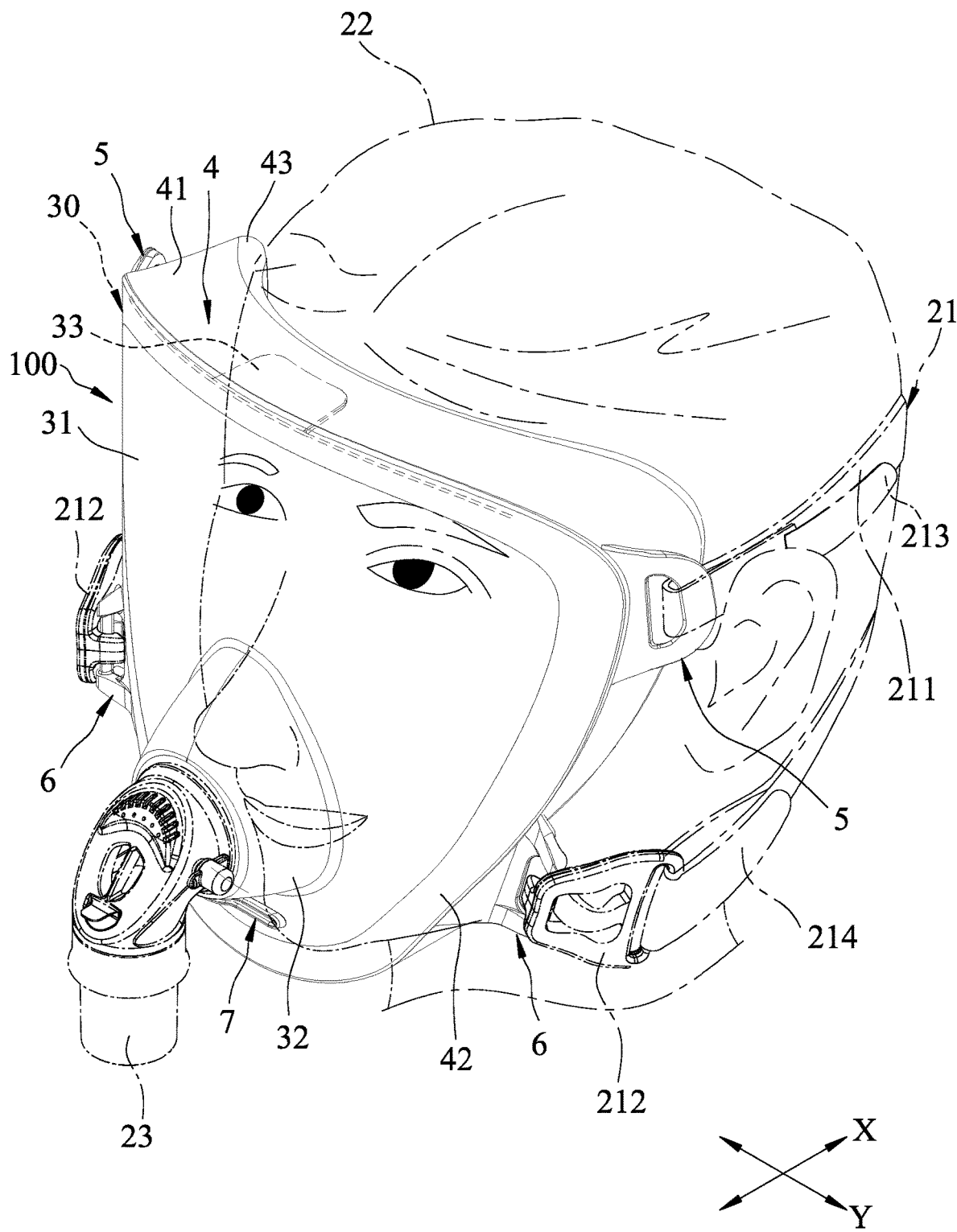
FIG. 3 is a perspective view of a full face respirator mask according to the first embodiment of the present disclosure in a state of use.
Figure 4:
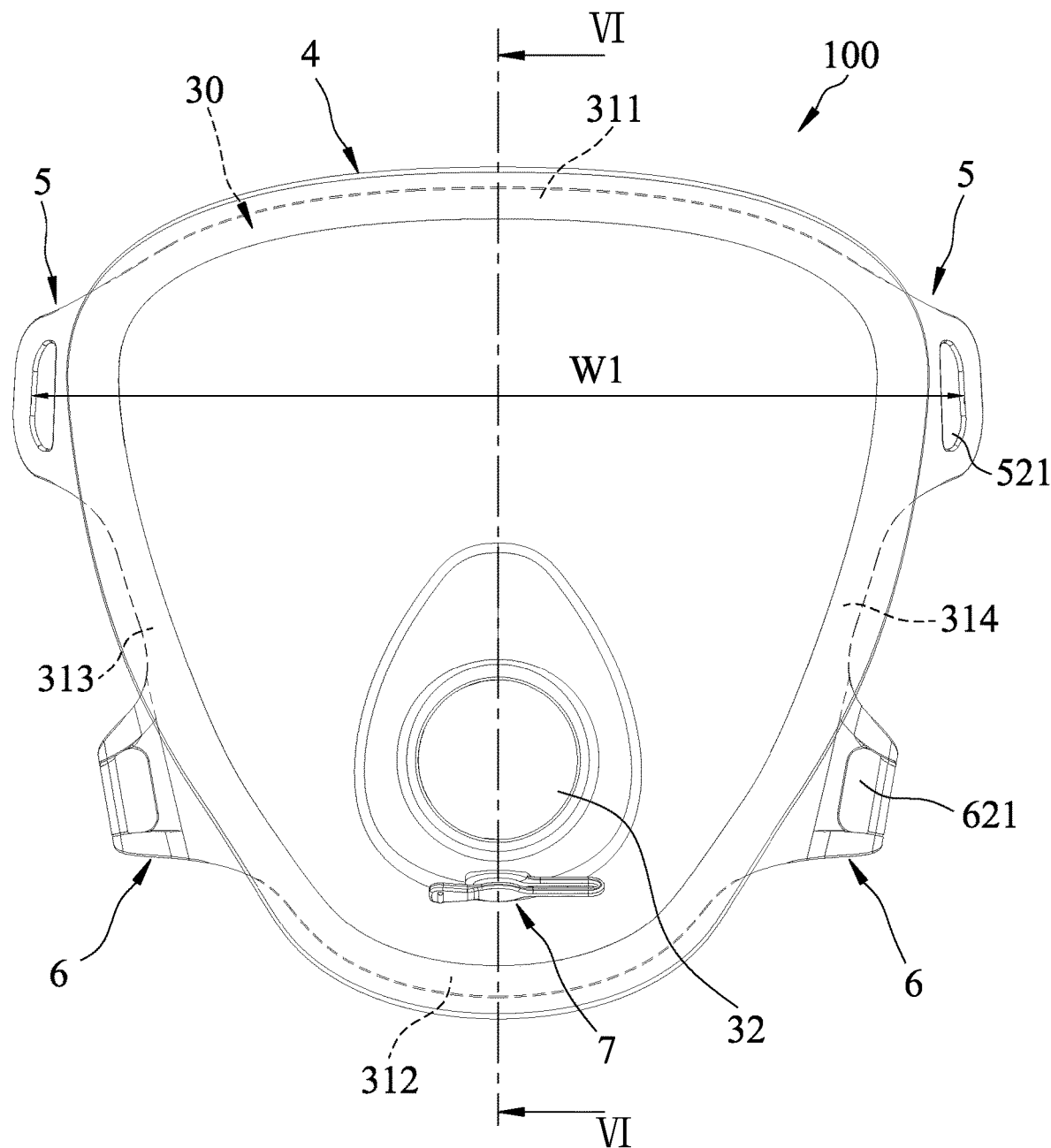
FIG. 4 is a front view of the first embodiment.
Figure 5:
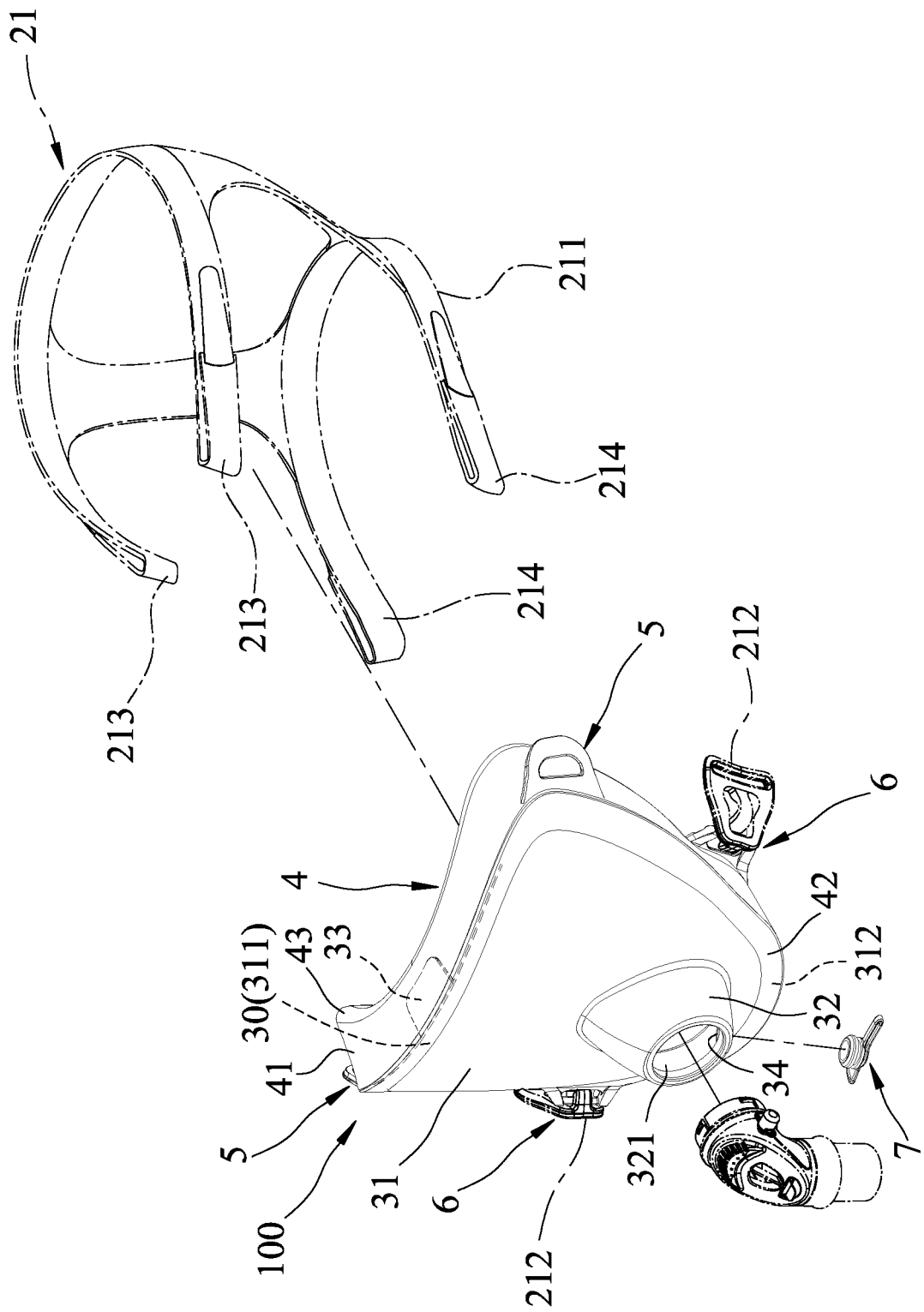
FIG. 5 is a perspective view of the first embodiment prior to connection with a positive pressure respirator and a head strap unit.
Figure 6:
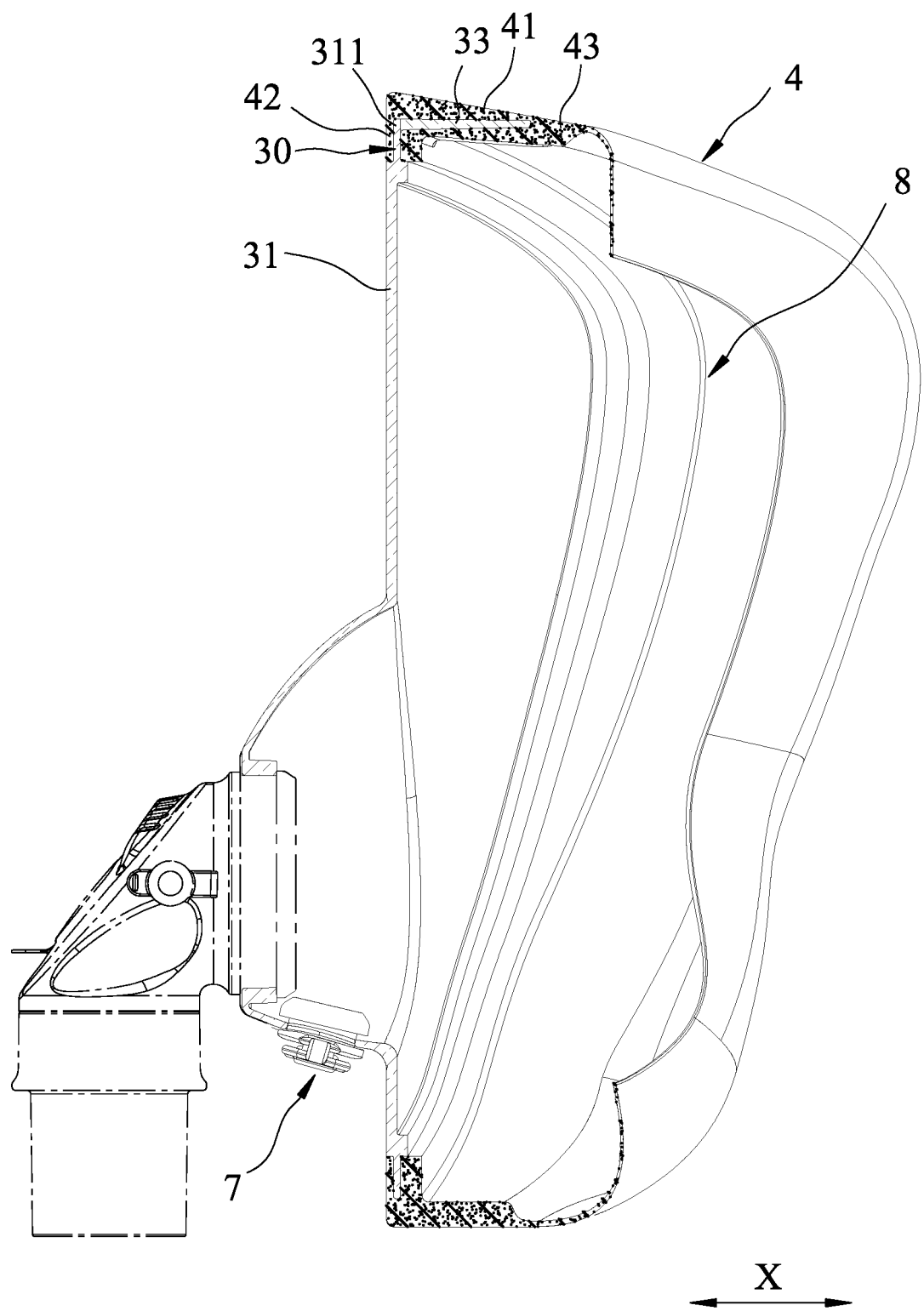
FIG. 6 is a sectional view of the first embodiment taken along line VI-VI of FIG. 4.

Before the present disclosure is described in greater detail with reference to the accompanying embodiments, it should be noted herein that like elements are denoted by the same reference numerals throughout the disclosure.

Referring to FIGS. 3 to 7, a full face respirator mask 100 according to the first embodiment of the present disclosure is suitable for connection with a head strap unit 21 to fix the full face respirator mask 100 to the face of the user 22, and is suitable for connection with a positive pressure respirator 23. The head strap unit 21 includes a strap body 211 and two engaging fasteners 212. The strap body 211 includes two upper straps 213 and two lower straps 214. The engaging fasteners 212 are respectively connected to the lower straps 214. The full face respirator mask 100 comprises a ring-shaped frame 30, a transparent face plate 31, a cushion 4, two upper connectors 5, two lower connectors 6, and a plug member 7.

The ring-shaped frame 30 includes a top part 311 corresponding to the forehead of the user 22, a bottom part 312 opposite to the top part 311 and corresponding to the chin of the user 22, and a left part 313 and a right part 314 connected between the top part 311 and the bottom part 312 and respectively corresponding to two cheeks of the user 22. In this embodiment, the ring-shaped frame 30 further has a protruding plate 33 extending rearwardly and horizontally from the top part 311.

The transparent face plate 31 is connected to an inner periphery of the ring-shaped frame 30.

A hollow front protruding portion 32 extends forwardly from a central portion of the face plate 31, and is located in a position corresponding to the nose and mouth of the user. The front protruding portion 32 has a guide hole 34.

An air inlet 321 extends through the front protruding portion 32 and the face plate 31 along a front-rear direction (X) for connection with the positive pressure respirator 23. The guide hole 34 communicates with the air inlet 321.

The cushion 4 is made of silicone, and is integrally molded to the ring-shaped frame 30. The cushion 4 has a ring-shaped cushion body 41 cooperating with the cushion body 41 to define a receiving space 8 communicating with the air inlet 32 and the guide hole 34. The cushion body 41 includes a ring-shaped flange 42 extending inwardly from an outer peripheral end of the cushion body 41 and embedding an outer periphery of the ring-shaped frame 30, and a ring-shaped abutment portion 43 extending inwardly from an inner peripheral end of the cushion body 41 and opposite to the ring-shaped flange 42 for abutting against the face of the user 22.

Figure 7:
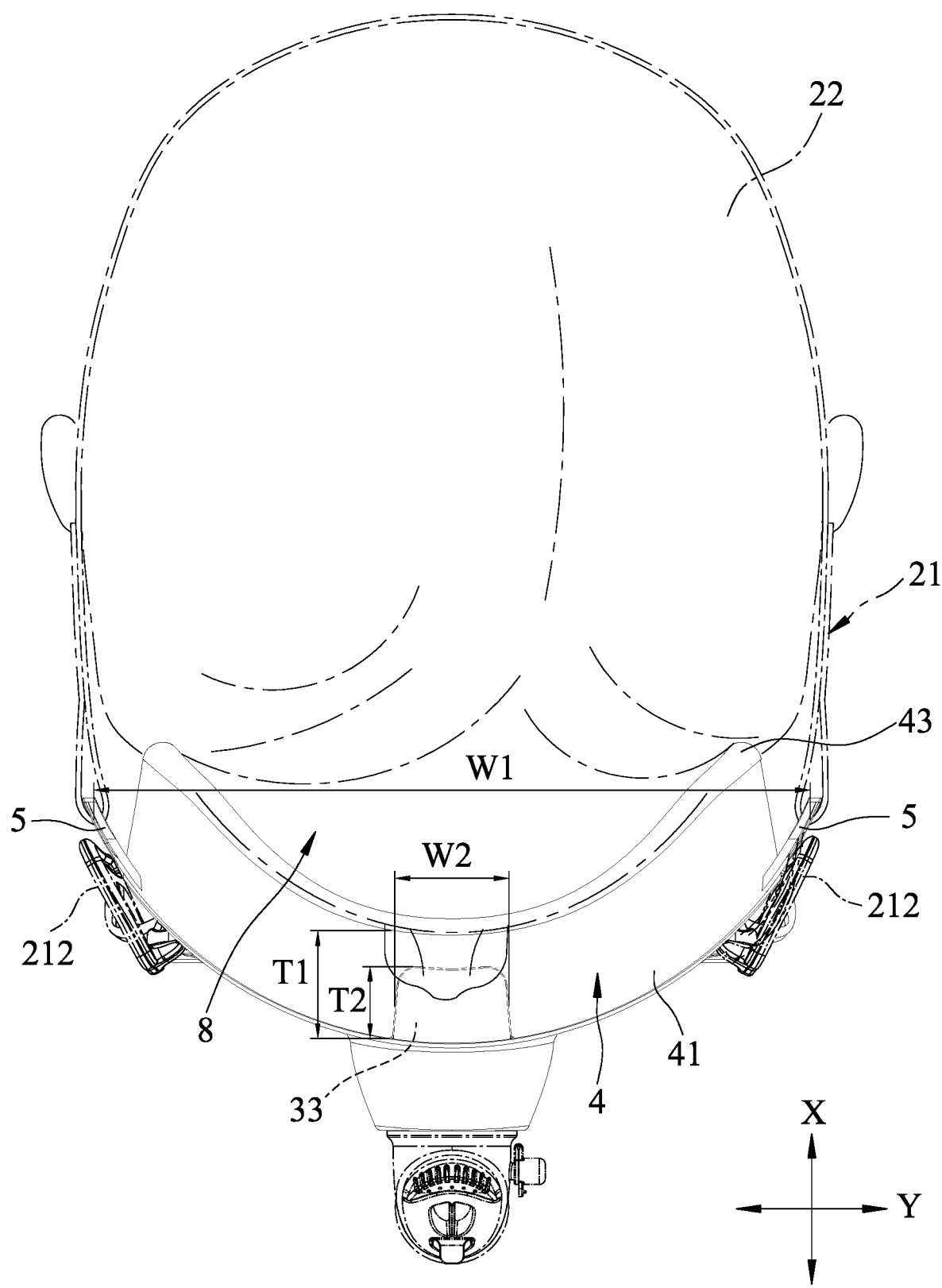
FIG. 7 is a top view of FIG. 3.

With reference to FIG. 7, a width of the cushion body 41 along the front-rear direction (X) is defined as T1, and a length of the protruding plate 33 along the front-rear direction (X) is defined as T2. The ratio of T2 to T1 has a range of 50% to 90%.

The upper connectors 5 extend outwardly and respectively from the left and right parts 313, 314 of the ring-shaped frame 30 in proximity to the top part 311, and are located externally of the cushion 4. Each upper connector 5 has a first engaging hole 521. The first engaging holes 521 of the upper connectors 5 are configured to connect with the upper straps 213 of the head strap unit 21 in a conventional manner.

The maximum width between the first engaging holes 521 of the upper connectors 5 along a transverse direction (Y) transverse to the front-rear direction (X) is defined as W1, while a width of the protruding plate 33 along the transverse direction (Y) is defined as W2. The ratio of W2 to W1 has a range of 6% to 28%, preferably 17% to 28%.

The lower connectors 6 extend outwardly and respectively from the left and right parts 313, 314 of the ring-shaped frame 30 in proximity to the bottom part 312, and are located externally of the cushion 4. Each lower connector 6 has a second engaging hole 621. The second engaging holes 621 of the lower connectors 6 are configured to connect with the lower straps 214 of the head strap unit 21 in the conventional manner.

The plug member 7 is used to removably close the guide hole 34 in the front protruding portion 32.

During manufacture of the full face respirator mask 100, the ring-shaped frame 30, the upper connectors 5 and lower connectors 6 are first integrally formed as one piece from plastic, after which the cushion 4 is integrally molded as one piece to the ring-shaped frame 30.

In use, the upper straps 213 are respectively inserted through the first engaging holes 521, and the engaging fasteners 212 are respectively engaged to the second engaging holes 621, so that the abutment portion 43 of the cushion body 41 abuts against the face of the user 22, and the face of the user 22 is received in the receiving space 8. The upper straps 213 and the lower straps 214 are then adjusted to increase or decrease the tension applied to the ring-shaped frame 30 through the upper and lower connectors 5, 6 so as to fix and position the full face respirator mask 100 to the face of the user 22. Finally, the positive pressure respirator 23 is connected to the air inlet 32, and is operated to supply pressurized gas body, such as air, oxygen, etc., into the receiving space 8 via the air inlet 32 for the user 22 to use.

With the protruding plate 33 embedded in the cushion body 41, when the upper and lower straps 213, 214 apply tension to the ring-shaped frame 30 through the upper and lower connectors 5, 6, the protruding plate 33 can push a central top portion of the abutment portion 43 to abut tightly against the forehead of the user 22, so that the force received by the cushion body 41 is uniform, and the abutment portion 43 will not be affected by the gas pressure and will not deform to create a gap. Thus, leakage of the gas body can be prevented. Further, the cushion body 41 can be stably positioned on the face of the user 22 without having to adjust the upper and lower straps 213, 214 and increase the tension applied to the ring-shaped frame 30.

Moreover, when the full face respirator mask 100 is used, and if it is necessary to insert a guide tube (not shown) simultaneously, the plug member 7 can be removed from the guide hole 34 to permit insertion of the guide tube into the receiving space 8 through the guide hole 34 for the user 22 to use.

It is worth to mention herein that, in this embodiment, the ring-shaped frame 30, the upper connectors 5 and the lower connectors 6 are first integrally formed as one piece from plastic, after which the cushion 4 is integrally molded as one piece to the assembly of the ring-shaped frame 30 and the upper and lower connectors 5, 6. In other variations, the foregoing components may first be manufactured individually, after which they are connected together. As long as the cushion 4 can be airtightly connected to the ring-shaped frame 30 so that the receiving space 8 can be maintained in an airtight state, any method is acceptable.

Figure 8:
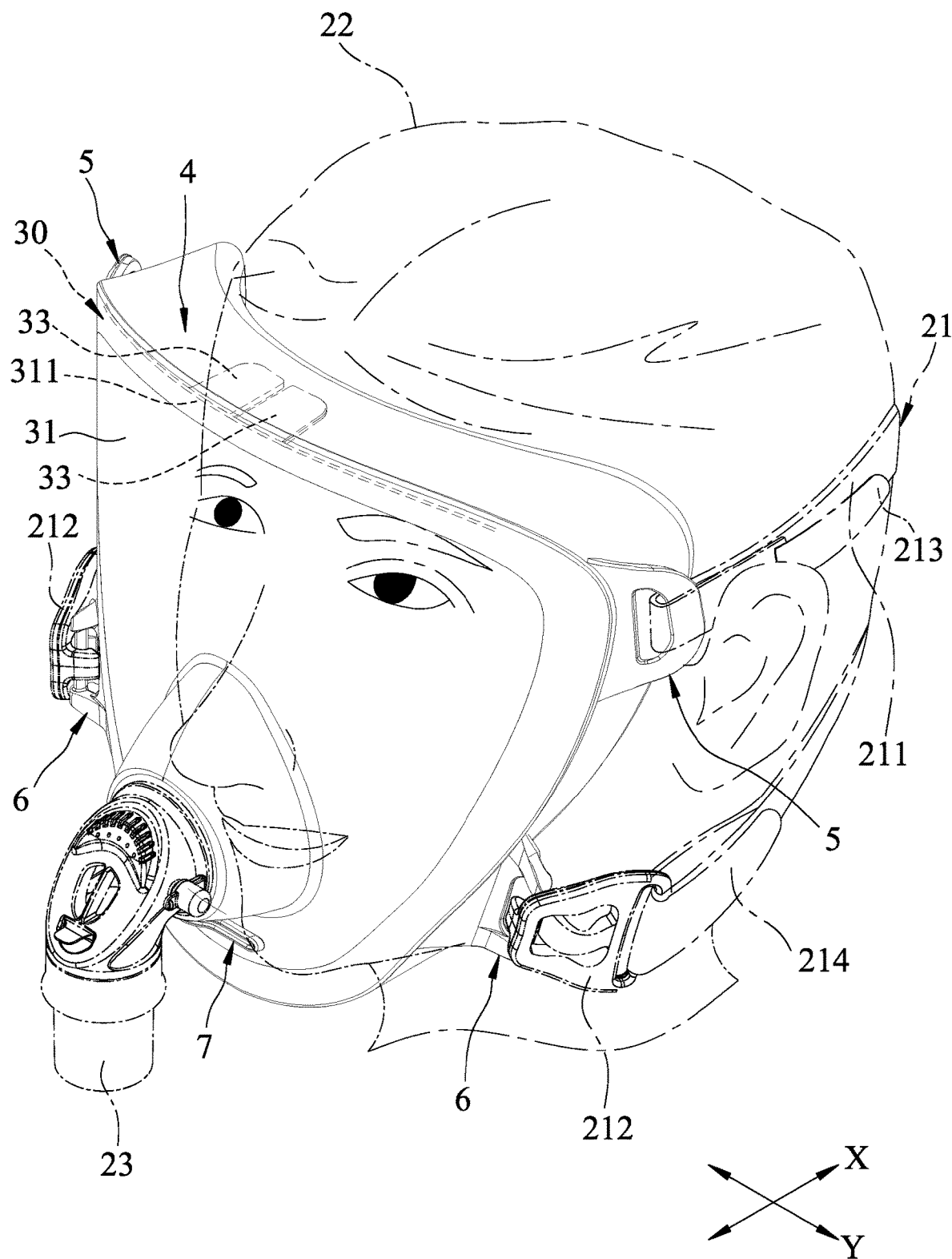
FIG. 8 is a perspective view of a full face respirator mask according to the second embodiment of this disclosure.
Figure 9:
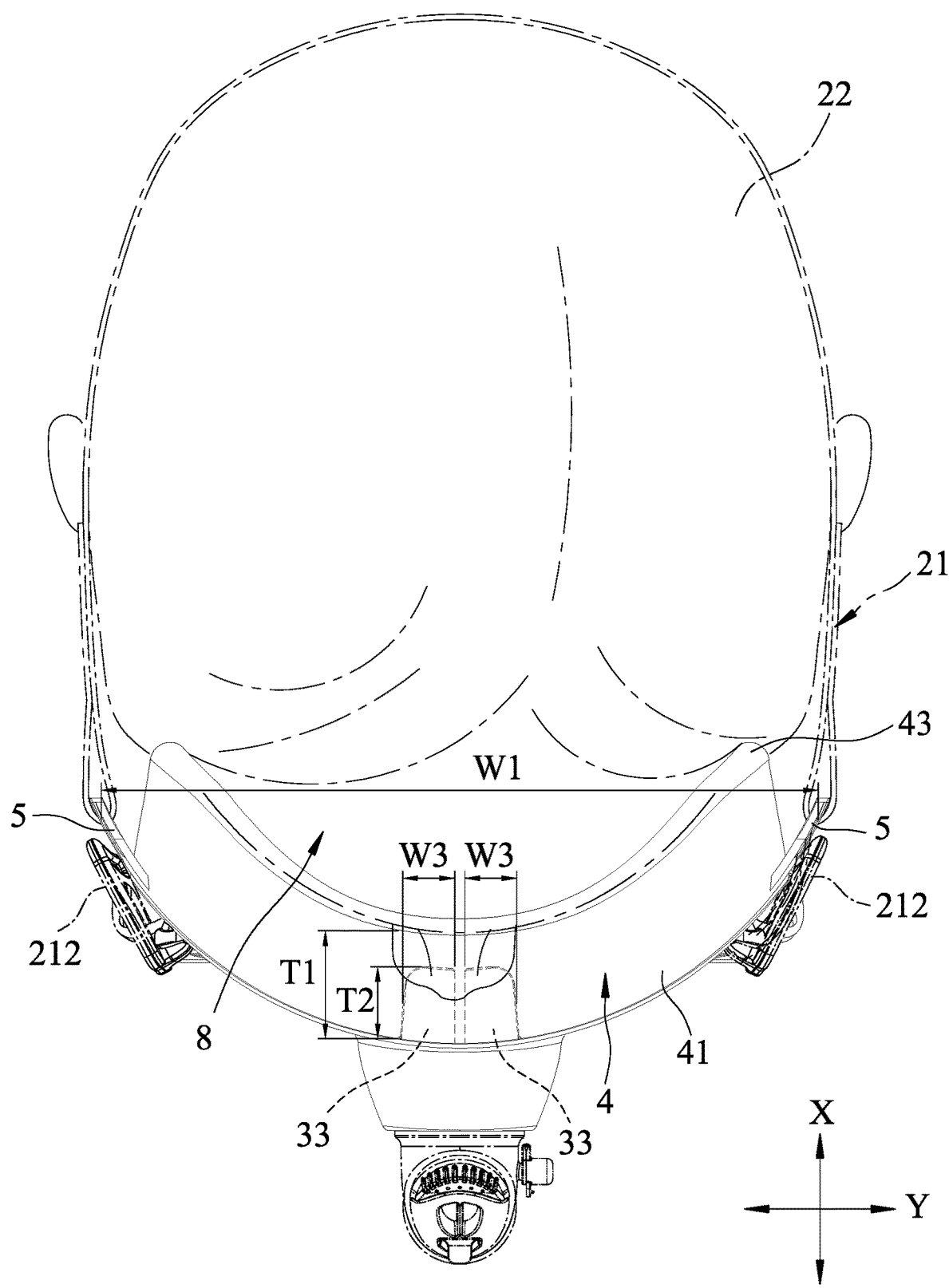
FIG. 9 is a top view of FIG. 8.

Referring to FIGS. 8 and 9, the second embodiment of the full face respirator mask 100 of this disclosure is similar to the first embodiment, and only differs in that the ring-shaped frame 30 of the second embodiment has two protruding plates 33 extending rearwardly and horizontally from the top part 311 thereof and spaced apart from each other along the transverse direction (Y). The width of each protruding plate 33 along the transverse direction (Y) is defined as W3. The ratio of the sum of the widths (W3) of the protruding plates 33 to the maximum width (W1) between the first engaging holes 521 of the upper connectors 5 has a range of 6% to 28%. The sum of the widths (W3) of the protruding plates 33 is smaller than 6 cm. Through this, the second embodiment can also achieve an effect similar to the first embodiment.

It is worth to mention herein that the number of the protruding plates 33 in the second embodiment is two. However, in other implementations, the number of the protruding plates 33 may be more than three. As long as the sum of the widths of the protruding plates 33 along the transverse direction (Y) is smaller than 6 mm, and the ratio of the sum of the widths of the protruding plates 33 along the transverse direction (Y) to the maximum width (W1) between the first engaging holes 521 has a range of 6% to 28%, any number of the protruding plate 33 is acceptable.

In sum, with the protruding plate(s) 33 embedded in the cushion body 41, the protruding plate(s) 33 can press the abutment portion 43 to abut stably against the forehead of the user 22 when the upper and lower straps 213, 214 of the head strap unit 21 apply tension to the ring-shaped frame 30 through the upper and lower connectors 5, 6, so that the full face respirator mask 100 can be fixed and positioned to the face of the user 22. During this time, the abutment portion 43 will not be affected by the gas pressure, and will not deform to create a gap, so that leakage of the gas body can be prevented. Therefore, the object of this disclosure can indeed be achieved.

In the description above, for the purposes of explanation, numerous specific details have been set forth in order to provide a thorough understanding of the embodiments. It will be apparent, however, to one skilled in the art, that one or more other embodiments maybe practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A full face respirator mask, comprising:
    a ring-shaped frame having a top part corresponding to the forehead of a user, a bottom part opposite to said top part and corresponding to the chin of the user, and a left part and a right part connected between said top part and said bottom part and respectively corresponding to two cheeks of the user, said ring-shaped frame further having at least one protruding plate extending rearwardly and horizontally from said top part;
    a transparent face plate connected to an inner periphery of said ring-shaped frame;
    an air inlet extending through said transparent face plate in a front-rear direction for connection with a positive pressure respirator;
    a cushion made of silicone and integrally molded to said ring-shaped frame, said cushion having a ring-shaped cushion body cooperating with said transparent face plate to define a receiving space which communicates with said air inlet, said cushion body including a ring-shaped abutment portion extending inwardly from an inner peripheral end of said cushion body for abutting against the face of the user; and
    two upper connectors extending outwardly and respectively from said left and right parts in proximity to said top part and located externally of said cushion, each of said upper connectors having a first engaging hole for connection with a head strap unit;
    wherein said at least one protruding plate is embedded in said cushion body to push said abutment portion to abut tightly against the face of the user when said full face respirator mask is positioned on the face of the user; and
    wherein the maximum width between said first engaging holes of said upper connectors along a transverse direction transverse to the front-rear direction is defined as W1, and a width of said at least one protruding plate along the transverse direction is defined as W2, the ratio of W2 to W1 having a range of 6% to 28%.

2. The full face respirator mask as claimed in claim 1, wherein said cushion body further includes a ring-shaped flange opposite to said abutment portion and embedding an outer periphery of said ring-shaped frame.

3. The full face respirator mask as claimed in claim 1, wherein a width of said cushion body along the front-rear direction (X) is defined as T1, and a length of said at least one protruding plate along the front-rear direction (X) is defined as T2, the ratio of T2 to T1 having a range of 50% to 90%.

4. The full face respirator mask as claimed in claim 1, wherein the ratio of W2 to W1 has a range of 17% to 28%.

5. The full face respirator mask as claimed in claim 1, further comprising two lower connectors extending outwardly and respectively from said left and right parts in proximity to said bottom part and located externally of said cushion for connection with the head strap unit.

6. The full face respirator mask as claimed in claim 5, wherein said ring-shaped frame, said upper connectors and said lower connectors are integrally formed as one piece from plastic.

7. The full face respirator mask as claimed in claim 1, further comprising a hollow front protruding portion extending forwardly from a central portion of said transparent face plate and located in a position corresponding to the nose and mouth of the user, said air inlet extending through said front protruding portion along the front-rear direction, said front protruding portion having a guide hole communicating with said air inlet, said full face respirator mask further comprising a plug member that removably closes said guide hole.

8. A full face respirator mask, comprising:
    a ring-shaped frame having a top part corresponding to the forehead of a user, a bottom part opposite to said top part and corresponding to the chin of the user, and a left part and a right part connected between said top part and said bottom part and respectively corresponding to two cheeks of the user, said ring-shaped frame further having at least one protruding plate extending rearwardly and horizontally from said top part;
    a transparent face plate connected to an inner periphery of said ring-shaped frame;
    an air inlet extending through said transparent face plate in a front-rear direction for connection with a positive pressure respirator;
    a cushion made of silicone and integrally molded to said ring-shaped frame, said cushion having a ring-shaped cushion body cooperating with said transparent face plate to define a receiving space which communicates with said air inlet, said cushion body including a ring-shaped abutment portion extending inwardly from an inner peripheral end of said cushion body for abutting against the face of the user; and two upper connectors extending outwardly and respectively from said left and right parts in proximity to said top part and located externally of said cushion, each of said upper connectors having a first engaging hole for connection with a head strap unit;

wherein said at least one protruding plate is embedded in said cushion body to push said abutment portion to abut tightly against the face of the user when said full face respirator mask is positioned on the face of the user; and wherein the maximum width between said first engaging holes of said upper connectors along a transverse direction transverse to the front-rear direction is defined as $W1$, said at least one protruding plate including a plurality of protruding plates extending rearwardly from said top part along the front-rear direction and spaced apart from each other along the transverse direction, the sum of the widths of said protruding plates along the transverse direction being smaller than 6 cm, the ratio of the sum of the widths of said protruding plates to the maximum width between said first engaging holes having a range of 6% to 28%.

* * * * *